(12) United States Patent
Williams, Jr. et al.

(10) Patent No.: US 8,626,342 B2
(45) Date of Patent: Jan. 7, 2014

(54) DATA COLLECTION DEVICE, SYSTEM, METHOD, AND COMPUTER PROGRAM PRODUCT FOR COLLECTING DATA RELATED TO THE DISPENSING OF CONTRAST MEDIA

(75) Inventors: Robert C. Williams, Jr., Fort Salonga, NY (US); Steven Hartman, Commack, NY (US); Tito Tengco, Dix Hills, NY (US); Clark Godfrey, East Northport, NY (US); Alan Cross-Hansen, Massapequa Park, NY (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 1530 days.

(21) Appl. No.: 11/259,953

(22) Filed: Oct. 27, 2005

(65) Prior Publication Data

US 2006/0089544 A1  Apr. 27, 2006

Related U.S. Application Data

(60) Provisional application No. 60/622,477, filed on Oct. 27, 2004.

(51) Int. Cl.
*A61B 5/00* (2006.01)
(52) U.S. Cl.
USPC ............ 700/266; 702/19; 702/22; 702/23; 702/30; 702/31; 702/32; 600/300
(58) Field of Classification Search
USPC .......... 700/266; 600/300; 702/19, 22, 23, 30, 702/31, 32
See application file for complete search history.

(56) References Cited

U.S. PATENT DOCUMENTS 3,631,847 A   1/1972 Hobbs
3,701,345 A   10/1972 Heilman et al.
(Continued)

FOREIGN PATENT DOCUMENTS

CN   1491730 A   4/2004
EP   1 182 613 A   2/2002
(Continued)

OTHER PUBLICATIONS

Ezem, Inc; "There is only one choice in CT injector systems"; pp. 1-8; Copyright 1995, E-Z-EM, Inc.

(Continued)

*Primary Examiner* — Brian R Gordon
*Assistant Examiner* — Shogo Sasaki
(74) *Attorney, Agent, or Firm* — Fredrikson & Byron, P.A.

(57) ABSTRACT

The present invention comprises devices, systems, methods, and computer program products for managing data related to the dispensing of contrast media as part of a medical procedure. The device and system provide a controller that is capable of communicating with a dispensing device so as to extract, arrange, process, and present a data set (e.g., a usage data set) from the dispensing device to a user such that the user may selectively monitor statistics related to the administration of contrast media, saline, or other consumables used during one or more dispensing operations. The method and computer program product for managing data related to the dispensing of contrast media may further allow for extraction, arrangement, processing, and presentation of the data set via the controller, via a user interface that is operably engaged with the dispensing device and/or via a computer network that may be in communication with the dispensing device.

21 Claims, 9 Drawing Sheets

(56) References Cited

U.S. PATENT DOCUMENTS

| | | | |
|---|---|---|---|
| 4,006,736 A | | 2/1977 | Kranys et al. |
| 4,477,923 A | * | 10/1984 | Baumann et al. ............... 378/95 |
| 4,650,465 A | | 3/1987 | Langer et al. |
| 4,695,271 A | | 9/1987 | Goethel |
| 4,854,324 A | | 8/1989 | Hirschman et al. |
| 5,319,363 A | | 6/1994 | Welch et al. |
| 5,331,552 A | * | 7/1994 | Lloyd et al. ..................... 378/15 |
| 5,662,612 A | | 9/1997 | Niehoff |
| 5,681,286 A | | 10/1997 | Niehoff |
| 5,868,710 A | | 2/1999 | Battiato et al. |
| 5,885,245 A | | 3/1999 | Lynch et al. |
| 6,004,285 A | | 12/1999 | Sugahara |
| 6,167,293 A | * | 12/2000 | Chenevert et al. ............ 600/420 |
| 6,171,276 B1 | | 1/2001 | Lippe et al. |
| 6,195,579 B1 | * | 2/2001 | Carroll et al. ................. 600/420 |
| 6,230,041 B1 | * | 5/2001 | Prince ............................ 600/420 |
| 6,269,340 B1 | | 7/2001 | Ford et al. |
| 6,339,718 B1 | * | 1/2002 | Zatezalo et al. .............. 600/432 |
| 6,356,780 B1 | * | 3/2002 | Licato et al. .................. 600/407 |
| 6,375,624 B1 | * | 4/2002 | Uber et al. .................... 600/549 |
| 6,397,097 B1 | * | 5/2002 | Requardt ....................... 600/431 |
| 6,397,098 B1 | * | 5/2002 | Uber et al. .................... 600/431 |
| 6,408,201 B1 | * | 6/2002 | Foo et al. ...................... 600/410 |
| 6,487,428 B1 | * | 11/2002 | Culver et al. ................. 600/310 |
| 6,505,064 B1 | | 1/2003 | Liu et al. |
| 6,546,275 B2 | * | 4/2003 | Carroll .......................... 600/419 |
| 6,597,937 B2 | * | 7/2003 | Liu et al. ....................... 600/420 |
| 6,597,938 B2 | * | 7/2003 | Liu ................................ 600/420 |
| 6,741,880 B1 | * | 5/2004 | Foo et al. ...................... 600/419 |
| 6,757,417 B2 | * | 6/2004 | Licato et al. .................. 382/131 |
| 6,763,260 B2 | * | 7/2004 | Kohls ............................ 600/431 |
| 2002/0068865 A1 | * | 6/2002 | Meaney et al. ............... 600/415 |
| 2002/0172323 A1 | * | 11/2002 | Karellas et al. ................. 378/51 |
| 2003/0036674 A1 | * | 2/2003 | Bouton ............................ 600/12 |
| 2003/0036713 A1 | * | 2/2003 | Bouton et al. ................. 600/587 |
| 2003/0069498 A1 | * | 4/2003 | Kohls ............................ 600/431 |
| 2004/0064040 A1 | | 4/2004 | Masuda et al. |
| 2004/0102693 A1 | | 5/2004 | Jenkins |
| 2004/0172303 A1 | | 9/2004 | Declerck et al. |
| 2006/0074294 A1 | | 4/2006 | Williams et al. |
| 2006/0089544 A1 | | 4/2006 | Williams, Jr. et al. |
| 2007/0260213 A1 | * | 11/2007 | Williams et al. .............. 604/500 |
| 2009/0214094 A1 | * | 8/2009 | Williams et al. .............. 382/131 |

FOREIGN PATENT DOCUMENTS

| | | |
|---|---|---|
| EP | 1 439 482 A | 7/2004 |
| JP | 2001-245868 A | 9/2001 |
| JP | 2001-337998 A | 12/2001 |
| KR | 10-2009-0094389 | 9/2009 |
| WO | WO 03/059422 A1 | 7/2003 |

OTHER PUBLICATIONS

Ezem, Inc.; "PercuPump—Touch Screen CT Injector System"; Maintenance and Service Manual; Copyright 1996, E-Z-EM, Inc.; Item No. 1471152, Jun. 15, 1996; 81 Pages.

EZEM, Inc.; "PercuPump II—Touch Screen CT Injector System"; Manual and Operations Guide; Copyright 1995, E-Z-EM, Inc.; Item No. 1470891; 51 Pages.

Liebel-Flarsheim; Angiomat 6000 Contrast Delivery System Advertisement; 1992; Copyright 1992; 8 Pages.

Liebel-Flarsheim; Angiomat 6000 Digital Injection Systems, Installation and Service Manual, 601910; Jan. 1992.

Liebel-Flarsheim; Angiomat 6000 Digital Injection System, Parts Manual 601905; Jan. 1992.

Liebel-Flarsheim; Angiomat 6000 Digital Injection System, Part Manual 600995; Dec. 1991.

Liebel-Flarsheim; Angiomat CT Digital Injection System 115 V, Installation & Service Manual for M3 Models 600980; Dec. 1988.

Liebel-Flarsheim; Angiomat CT Digital Injection System Operator's Manual, 600964; Jul. 1990.

Liebel-Flarsheim; Angiomat CT Digital Injection System 115 V, Parts Manual 600977.

Liebel-Flarsheim, CT 9000 Contrast Delivery System Advertisement ;1992.

Liebel-Flarsheim, CT 9000 Digital Injection System Operator's Manual, 800950; 1995.

Liebel-Flarsheim, CT 9000 ADV Digital Injection System Operator's Manual, 800731-A, Nov. 1997.

Liebel-Flarsheim, CT 9000 ADV Digital Injection System Operator's Manual, 800731-B, Jul. 1998.

Liebel-Flarsheim, Angiographic & CT Injectors Adverstisement, 1992.

Office Action for Japan Application No. 2007-539101 dated Nov. 13, 2009.

International Preliminary Report on Patentability for International Appl. No. PCT/US2005/038741, issued May 1, 2007.

International Preliminary Report on Patentability for International Appl. No. PCT/US2008/061013, issued Oct. 27, 2009.

International Search Report for International Appl. No. PCT/US2005/038741, mailed Aug. 31, 2006.

International Search Report for International Appl. No. PCT/US2008/061013, mailed Sep. 8, 2008.

Office Action for Australian Patent Appl. No. 2005299297, mailed Dec. 17, 2008.

Office Action for Canadian Patent Appl. No. 2,584,521, mailed Jul. 23, 2010.

Office Action for Chinese Patent Appl. No. 200580040388.7, mailed Apr. 10, 2009.

Office Action for Chinese Patent Appl. No. 200580040388.7, mailed Aug. 6, 2010.

Office Action for Chinese Patent Appl. No. 200580040388.7, mailed Feb. 12, 2010.

Office Action for European Patent Appl. No. 05813778.7, mailed Feb. 11, 2008.

Office Action for European Patent Appl. No. 08746438.4, mailed Feb. 11, 2010.

Office Action for Japanese Patent Appl. No. 2007-539101, mailed Jun. 4, 2010.

Office Action for Japanese Patent Appl. No. 2007-539101, mailed Nov. 13, 2009.

Office Action for Korean Patent Appl. No. 10-2007-7012046, mailed Nov. 19, 2008.

Office Action for Korean Patent Appl. No. 10-2007-7012046, mailed Jul. 26, 2009.

Written Opinion for International Appl. No. PCT/US2008/061013, mailed Sep. 8, 2008.

Written Opinion for International Appl. No. PCT/US2005/038741, mailed Aug. 31, 2006.

Office Action for European Application No. 08746438.4 dated Sep. 22, 2010.

\* cited by examiner

DATA COLLECTION DEVICE, SYSTEM, METHOD, AND COMPUTER PROGRAM PRODUCT FOR COLLECTING DATA RELATED TO THE DISPENSING OF CONTRAST MEDIA

CROSS-REFERENCE TO RELATED APPLICATION

This application claims the benefit of U.S. Provisional Application No. 60/622,477, filed Oct. 27, 2004, which is incorporated by reference herein in its entirety.

FIELD OF THE INVENTION

The present invention relates generally to the collection of data related to the dispensing of media used during the course of a number of medical procedures. In one alternative embodiment, the present invention relates to the collection and archiving of data from an injector system and/or extravasation detection device such that clinical personnel and/or medical imaging practice managers may more readily access information relating to usage statistics of the injector system and/or extravasation detection device. In one alternative embodiment, the present invention provides a medical device, including, but not limited to a system, method, and/or computer program product that may be integrated into a medical imaging suite and in communication with one or more injector systems, one or more computer networks, and/or one or more extravasation detection devices so as to allow, for example, the analysis of statistics related to the usage of media, the usage of the injector systems, the usage of disposable accessories used in a medical procedure, for example, syringe components and/or the usage of the extravasation detection devices over the course of a selected time period, for example.

BACKGROUND OF THE INVENTION

Medical procedures, such as imaging procedures, often rely on the use of a media, such as contrast media, flushing media, or other liquid, solid, and/or gas media, that is dispensed and/or injected into the biological structure to be imaged such that the procedure provides more detailed information to a radiologist or other medical personnel responsible for analyzing the procedure results (such as medical imagery). Such medical imaging procedures may include, for instance, angiography, computed tomography (CT), ultrasound and/or NMR/MRI. The term "contrast media", as employed herein, refers to essentially any suitable type of media, as used in the medical arts, that is injected into an individual and, in the context of a medical procedure such as, for example an imaging procedure (such as MR, angiography, ultrasound or CT), facilitates in highlighting selected areas of the individual's body while the individual is being scanned. In addition, the term "contrast media", as employed herein, may also refer to other diagnostic or therapeutic agents for injection into individuals. The term "flushing media", as employed herein, refers to essentially any suitable type of medium, such as a saline solution, that can be used to flush contrast medium, or other types of materials, from the tubing of an infusion system (or any other components thereof) and that is well-suited for flowing through the individual's body so as to serve a useful supplementary purpose such as, for example, keeping his/her veins open in preparation for another infusion of contrast media. Contrast media may be injected into an individual's vasculature prior to a medical procedure (such as, for example, a medical imaging procedure) by a dispensing device including, but not limited to a power injector having an electronic controller.

Some dispensing devices may include electronic controllers capable of collecting and storing information related to the usage and/or function of the dispensing device. For instance, in some cases, the dispensing device may create a data set containing, for instance, information regarding volumes of contrast media dispensed, time and date stamps for particular medical procedures including, but not limited to medical imaging procedures, information related to the dispensing pressure exerted by the dispensing device during a particular dispensing operation (such as, for example, the pressure profile for a powered injection of contrast media) and/or information regarding the usage of sterile disposables (including syringes or other accessories used by the dispensing device).

In addition, in some medical imaging facilities, the dispensing device may be in communication with an extravasation detection accessory (EDA) (such as the E-Z-EM Extravasation Detection Accessory (EDA®)), or other accessory device capable of detecting extravasation events in an individual undergoing a medical imaging procedure. Such accessories may include, but are not limited to, adhesive electronic sensors capable of being adhered to an individual's skin at the contrast media injection site (in procedures using a power injector, for example). The EDA may thus be capable of detecting changes in impedance at the injection site corresponding to an extravasation event (which may include, for instance, cases wherein contrast media is inadvertently released outside the targeted injection area (i.e., outside the vasculature of the individual). EDA devices may include embedded electronic components that may be in communication with the electronic controller of the dispensing device, such that an operator of the dispensing device may choose whether or not to enable the EDA during a given dispensing operation. In addition, the EDA may generate a data set during the course of its operation during a dispensing operation. For instance, an EDA may, in some cases generate a data set that may be stored either in its embedded electronic components, or sent to the electronic controller of the dispensing device for storage along with the dispensing device data. Such EDA data may include but is not limited to, time and date stamps, an indication as to whether or not the EDA was enabled, and indication of whether or not an extravasation event was detected during a given dispensing operation, and an impedance profile (over time) generated by the EDA as it is adhered to an injection site.

Dispensing devices used in medical imaging practices may be syringe-based power injectors (including the E-Z-EM Empower CT® and Empower CTA® power injector systems) that may include one or more syringes (containing pre-loaded amounts of contrast media and/or saline solution). In addition, such systems may be electronically controlled via electronic controllers that may be pre-programmed to administer a variety of contrast media either arterially or intravenously in conjunction with medical imaging procedures. In addition, such automated, powered dispensing devices may also be in communication with an EDA that is capable of detecting an extravasation event and logging such an event (along with the corresponding impedance profile generated by the EDA) in either an embedded electronic component or with the electronic controller of the dispensing device.

The data sets generated, processed, and/or stored by the dispensing device (and/or its electronic controller), the EDA, and/or other accessory devices used to dispense and/or monitor the dispensing of contrast media in a medical imaging suite are currently stored in a manner that they may be accessible by a technician servicing the device such that the technician may be able to determine various types of information, including but not limited to the usage statistics and or error codes of the device. The data sets may not be stored and/or organized in a manner that would allow the data included therein to be used effectively by clinical professionals and/or other professionals charged with managing a medical imaging practice. On the contrary, medical practice managers and medical staff have conventionally relied on manual record-keeping methods to record and/or log the usage of contrast media and/or other statistics related to the usage of a dispensing device and/or EDA within a medical imaging practice. Thus, clinicians must take valuable time to manually collect usage statistics that may already be stored (in a relatively inaccessible and/or unhelpful format) within the electronic components of the devices within the medical imaging suite. In addition, clinical practice managers must rearrange the raw data taken by clinicians in order to convert the dispensing device and/or EDA usage statistics into a format that may be useful, from a business perspective, for assessing the efficiency of the medical imaging practices. For example, the clinical practice manager is often tasked with identifying sources of waste and with predicting budgetary needs for a given time period (i.e., instances of pre-loaded, but unused contrast media, the excessive use of disposables, and/or excessive instances of extravasation events (which may signal that a dispensing device is malfunctioning and/or requires servicing or replacement)).

Thus, there exists a need for a device, system, method, and/or computer program product capable of collecting, storing, processing, and/or arranging data sets from a medical device, including, but not limited to, a dispensing device or other medical imaging accessory such that data within the data sets (i.e., usage data sets) may be effectively used by a clinical practice manager to monitor the usage of contrast media, dispensing device usage, EDA usage, the usage of various disposables, and other usage data related to the dispensing of contrast media within a medical imaging suite. Also, there exists a need for a device capable of communicating with a medical device, including, but not limited to, a dispensing device, and/or a method and corresponding computer program product capable of operating on an electronic controller of such device that may collect, arrange, process, store, and/or effectively present data related to the operation of dispensing devices in a medical imaging suite.

SUMMARY OF THE INVENTION

The above and other needs are met by the present invention which, in one alternative embodiment, provides a data collection device adapted to be capable of communicating with a medical device, including but not limited to, a dispensing device configured to be capable of dispensing a contrast media as part of a medical procedure including, but not limited to, a medical imaging procedure. In one alternative embodiment, the data collection device comprises a controller adapted to be capable of communicating with a dispensing device and configured to be capable of transmitting and/or receiving a data set (such as, for example, a usage data set) from the dispensing device. In another alternative embodiment, the controller is further configured to be capable of arranging and modifying data within the data set, wherein the data within the data set is related to a dispensing operation of the dispensing device. The data collection device may also include a storage device configured to be in communication with the controller. In addition, the storage device may be configured to be capable of receiving the data within the data set such that data within the data set may be selectively retained.

In another alternative embodiment, the controller may be further adapted to be capable of communicating with an extravasation detection device (EDA). Also, the controller may be further configured to be capable of transmitting, receiving, or storing an extravasation data set from the EDA. According to such alternative embodiments, the storage device is further configured to be capable of receiving the data within the extravasation data set such that the extravasation data set is integrated with the data set selectively retained within the storage device. The controller may also, in some other alternative embodiments, be adapted to be capable of communicating with one or more supplemental electronic devices, including, but not limited to, a medical imaging device, a medical imaging device controller, a computer device and/or an electronic device that may be configured to be capable of producing supplemental data related to other aspects of a medical procedure, including but not limited to: a dispensing operation, an individual and/or patient history, and/or a medical imaging procedure, among other types of data.

In another alternative embodiment, the data collection device may further comprise a user interface that is capable of communicating with the storage device and the controller so as to enable a user of the data collection device to selectively access, modify, and/or supplement the data within the data set.

In another alternative embodiment of the present invention, a method and/or computer program product for collecting, storing, processing, and/or accessing a data set (such as, for example, a usage data set) related to the dispensing of contrast media is provided. In one alternative embodiment, the method comprises the steps of: collecting the data set from a medical device including, but not limited to a dispensing device; and directing the data set to a storage device such that data within the data set may be selectively retained therein. Here, the data sets may include, but are not limited to usage data sets, among other types of data. The method and computer program products of the invention may further comprise the steps of collecting an extravasation data set from an EDA wherein the data within the extravasation data set being related to a detection operation of the EDA performed during a medical imaging procedure, and directing the extravasation data set to the storage device such that the extravasation data set is integrated with the data set.

In another alternative embodiment, the method and/or computer program embodiments of the present invention may further comprise steps for: directing a portion of the data within a data set corresponding to an individual medical procedure (i.e., a medical imaging procedure) into a procedure data subset, arranging the procedure data subset by a date of the medical imaging procedure, and displaying data within the data set to a user via a user interface.

According to other method and/or computer program product embodiments of the present invention a host device may be in communication with one or more other medical devices, such as dispensing devices. In such embodiments, the method and computer program product embodiments of the present invention may further comprise steps which may include, but are not limited to: automatically synchronizing one or more data sets collected from the corresponding one or more devices; receiving a user-defined identifier for each of the one or more devices; selectively displaying data from at least one of the one or more data sets; storing the one or more data sets in a storage device; and automatically synchronizing the stored one or more data sets. Furthermore, some method and/or computer program embodiments adapted for use with one or more devices may comprise additional steps for: transferring at least one of the stored one or more data sets to at least one of the one or more devices so as to provide redundancy and/or data back-up capability, and exporting at least one of the one or more data sets to an alternate computer application for storage and/or analysis. Here, the device and data sets may include, but are not limited to a dispensing device and usage data sets, respectively.

Finally, some embodiments of the present invention provide a system for collecting, storing, processing, and accessing a data set (such as a usage data set, for example) related to the dispensing of contrast media as part of a medical procedure, including but not limited to a medical imaging procedure. Some system embodiments may comprise: means for collecting a data set (such as, for example, a usage data set) from a dispensing device, wherein the data within the data set may be related to a dispensing operation of the dispensing device; and means for directing the data set to a storage device. According to some system embodiments of the present invention, the storage device may be in communication with the dispensing device via a controller, and the storage device may be further adapted to selectively retain data within the data set. Other embodiments of the system of the present invention may further comprise means for collecting an extravasation data set from an extravasation detection device, wherein data within the extravasation data set may be related to a detection operation of the extravasation detection device performed during the medical procedure. The system may also comprise means for directing the extravasation data set to the storage device such that the extravasation data set may be integrated with the stored data set.

Furthermore, other system embodiments of the present invention may also comprise additional means for collecting, storing, processing, and/or arranging various data sets associated with the dispensing of contrast media as part of a medical imaging procedure. For example, the system may further comprise: means for collecting a supplemental data set from one or more supplemental electronic devices; means for directing the supplemental data set to the storage device such that the supplemental data set is integrated with the stored data set; means for directing a portion of the data within the stored data set into one or more procedure data subsets, each corresponding to an individual medical imaging procedure; means for arranging the one or more procedure data subsets by a date of the medical imaging procedure; and means for displaying data within the stored data set to a user.

According to other system embodiments of the present invention, the means for collecting usage data sets (or other data sets, such as data sets related to maintenance performed on a particular medical device, for example) (from a dispensing device and/or supplemental electronic device, for example) may further comprise means for collecting one or more data sets from a corresponding one or more dispensing devices. In some such embodiments, the system may further comprise: means for automatically synchronizing the one or more data sets; means for receiving a user-defined identifier for each of the one or more dispensing devices; means for selectively displaying data from at least one of the one or more data sets; means for storing the one or more data sets in a storage device; and means for automatically synchronizing the stored one or more data sets. Furthermore, some system embodiments may provide means for transferring at least one of the stored one or more data sets to at least one of the one or more dispensing devices for back-up and/or data redundancy within one or more dispensing devices in communication via a network. In addition some systems of the present invention may provide means for exporting at least one of the one or more data sets to an external computer application including, but not limited to: a word processing program; a spreadsheet program; a database program; a statistical analysis program; an inventory management program; an enterprise resource planning program; a radiology visualization program; and/or combinations thereof.

BRIEF DESCRIPTION OF THE DRAWINGS

Figure 1:
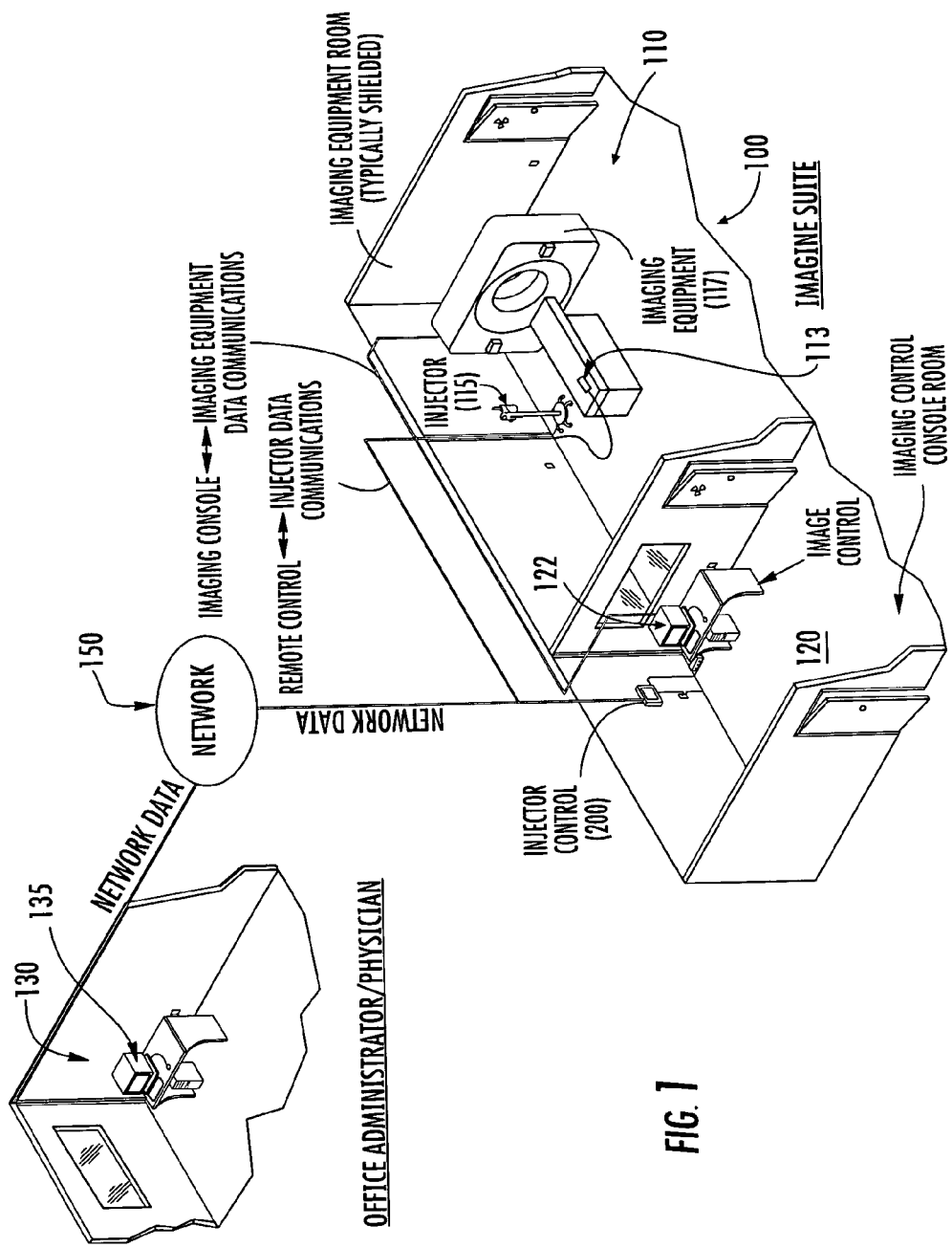
Figure 2:
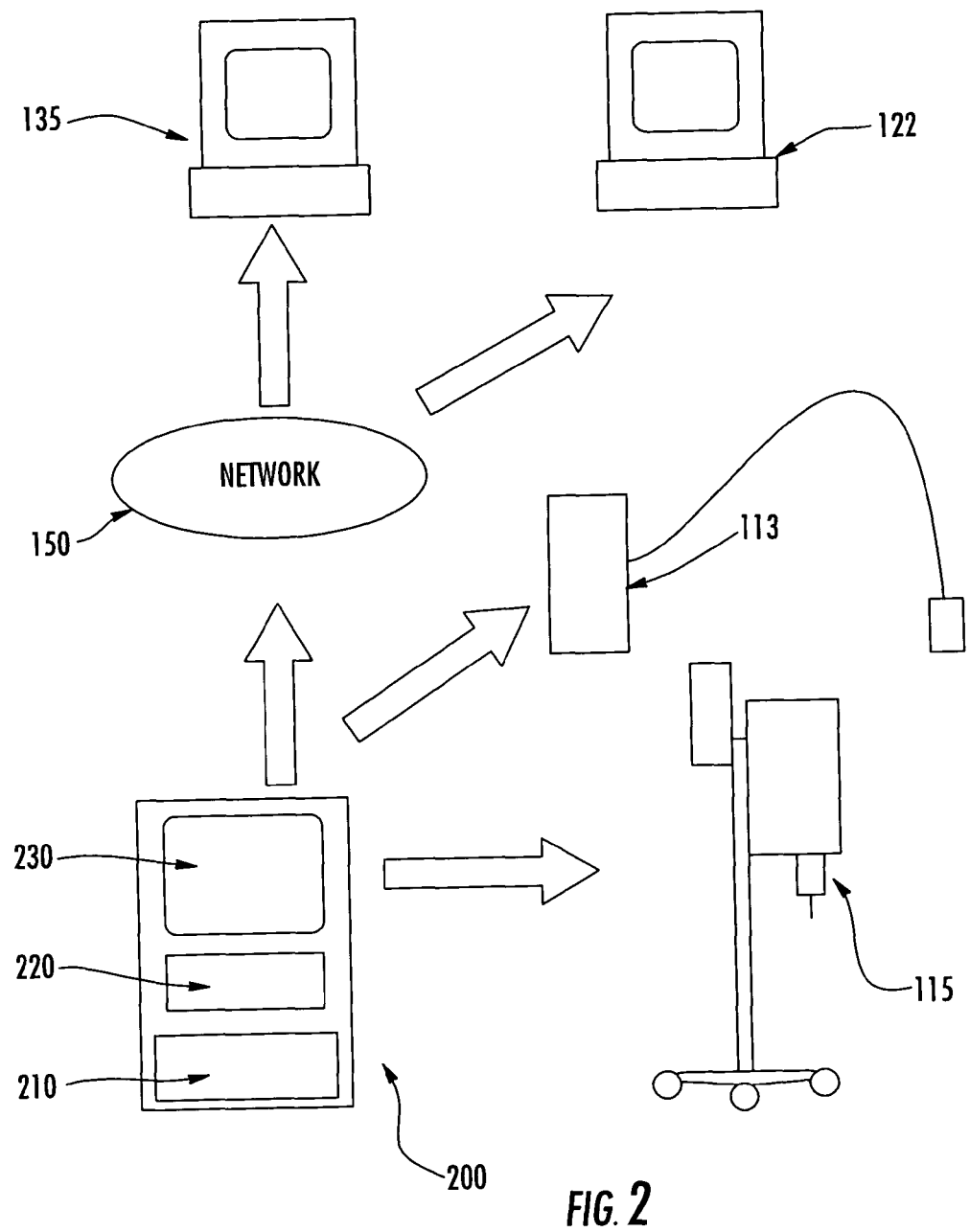
Figure 3:
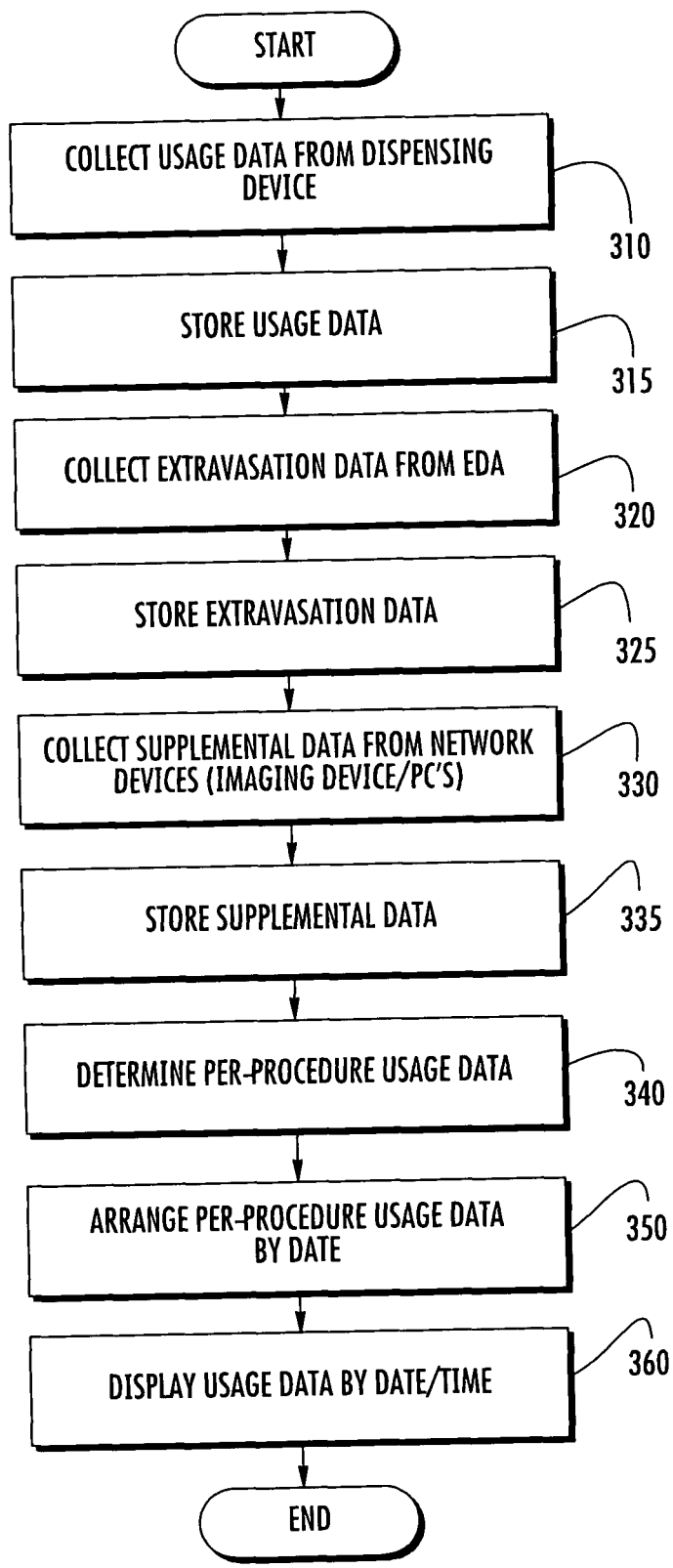
Figure 4:
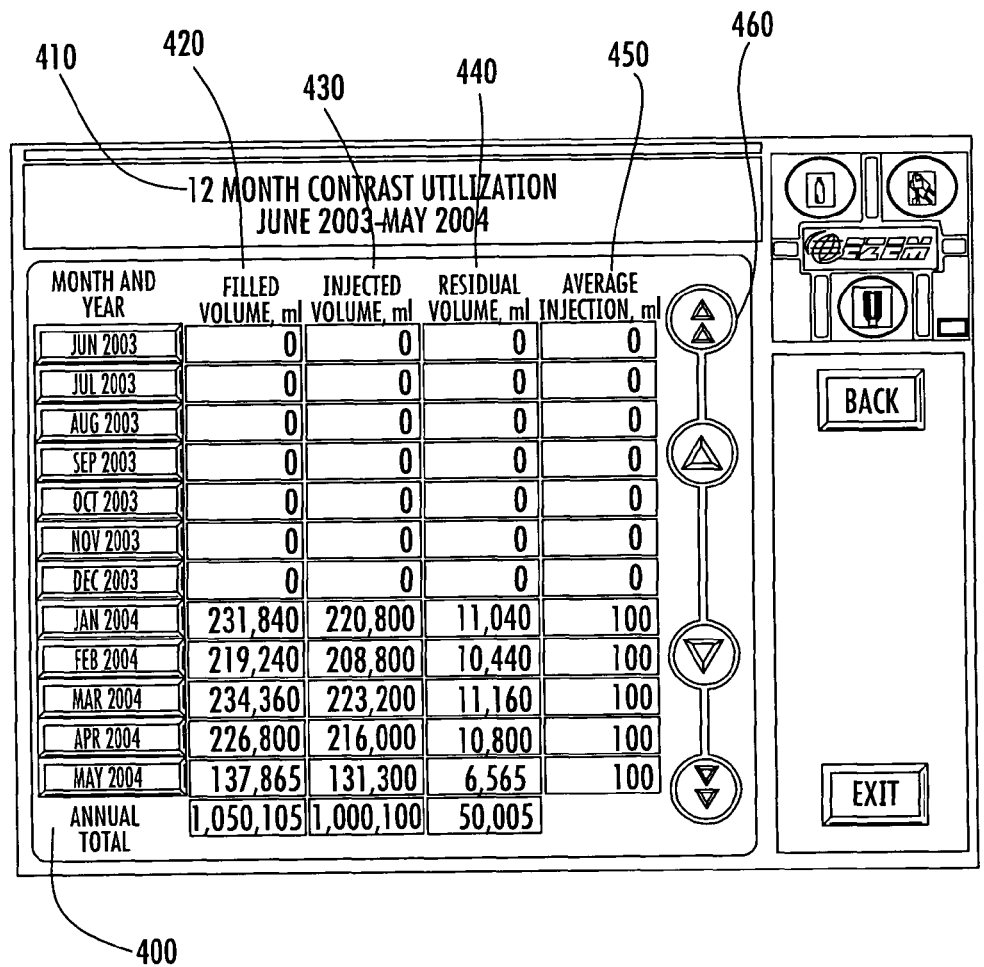
Figure 5:
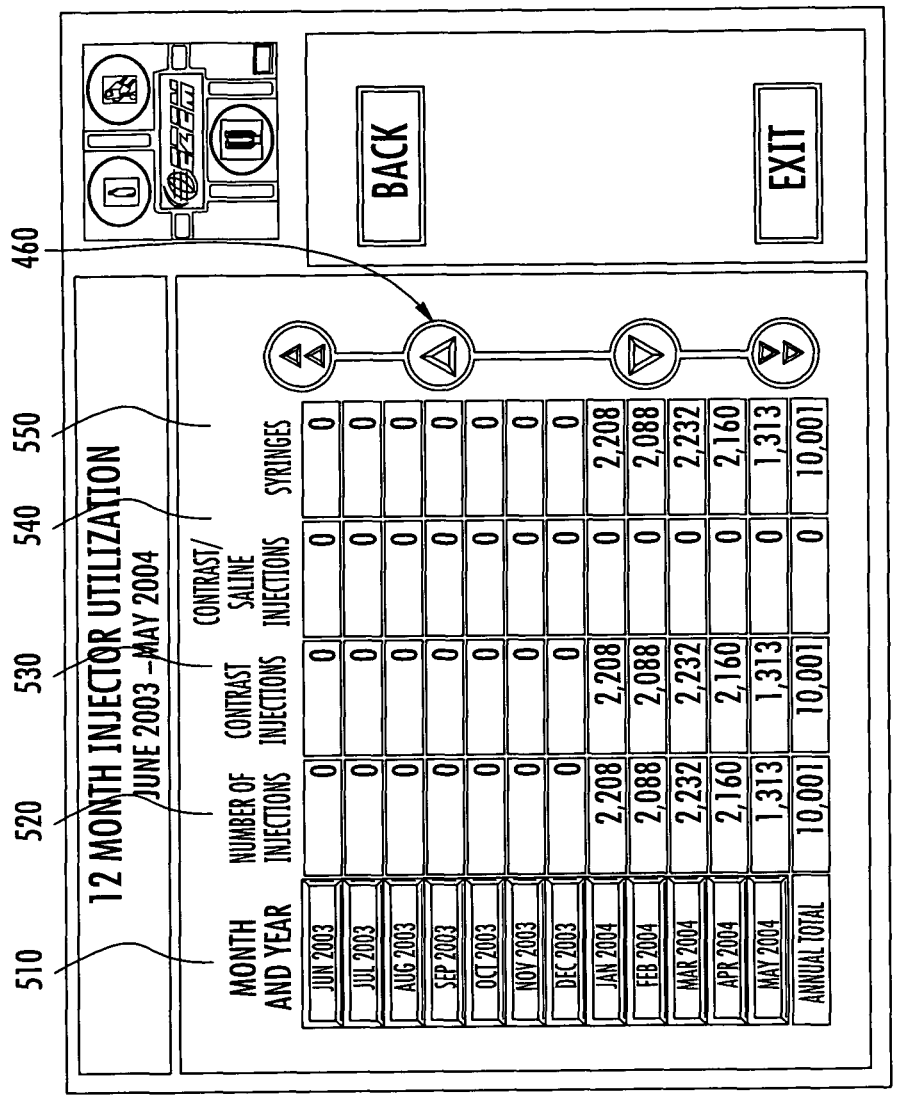
Figure 6:
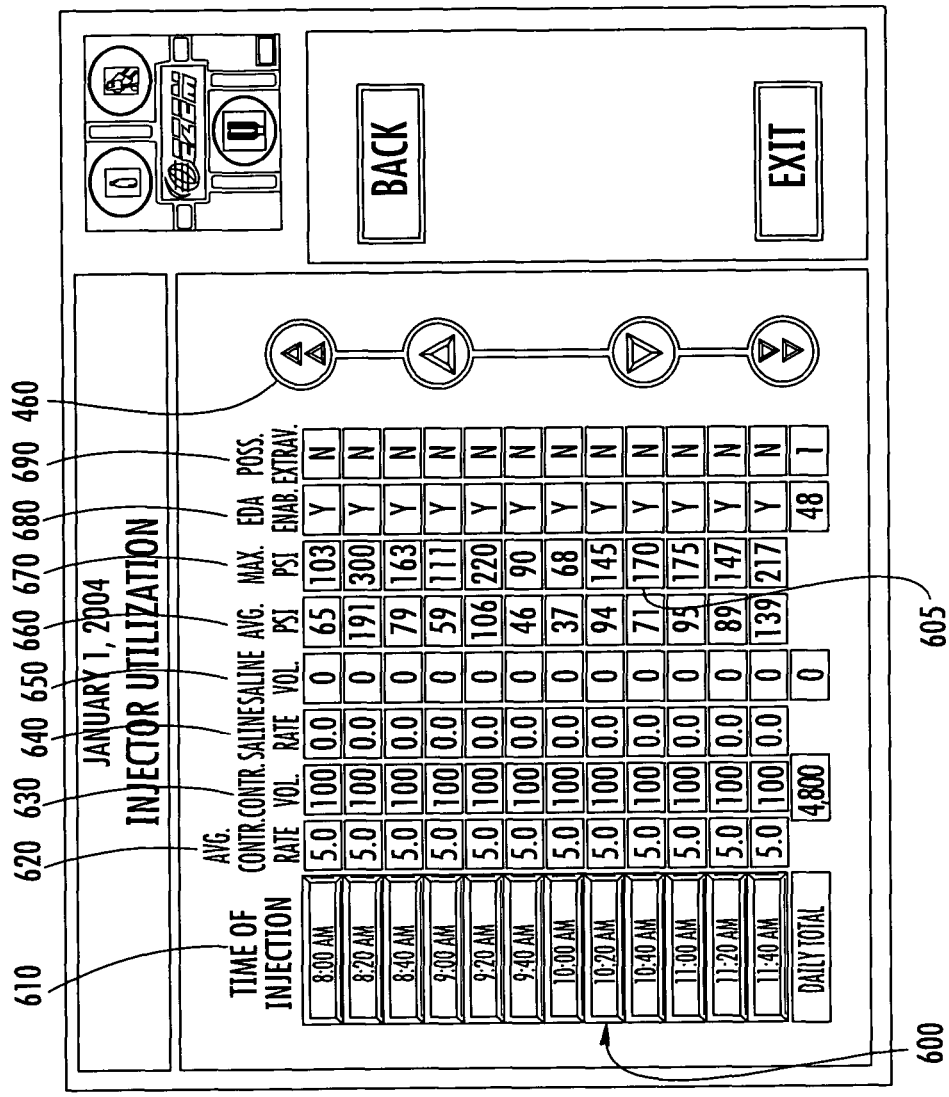
Figure 7:
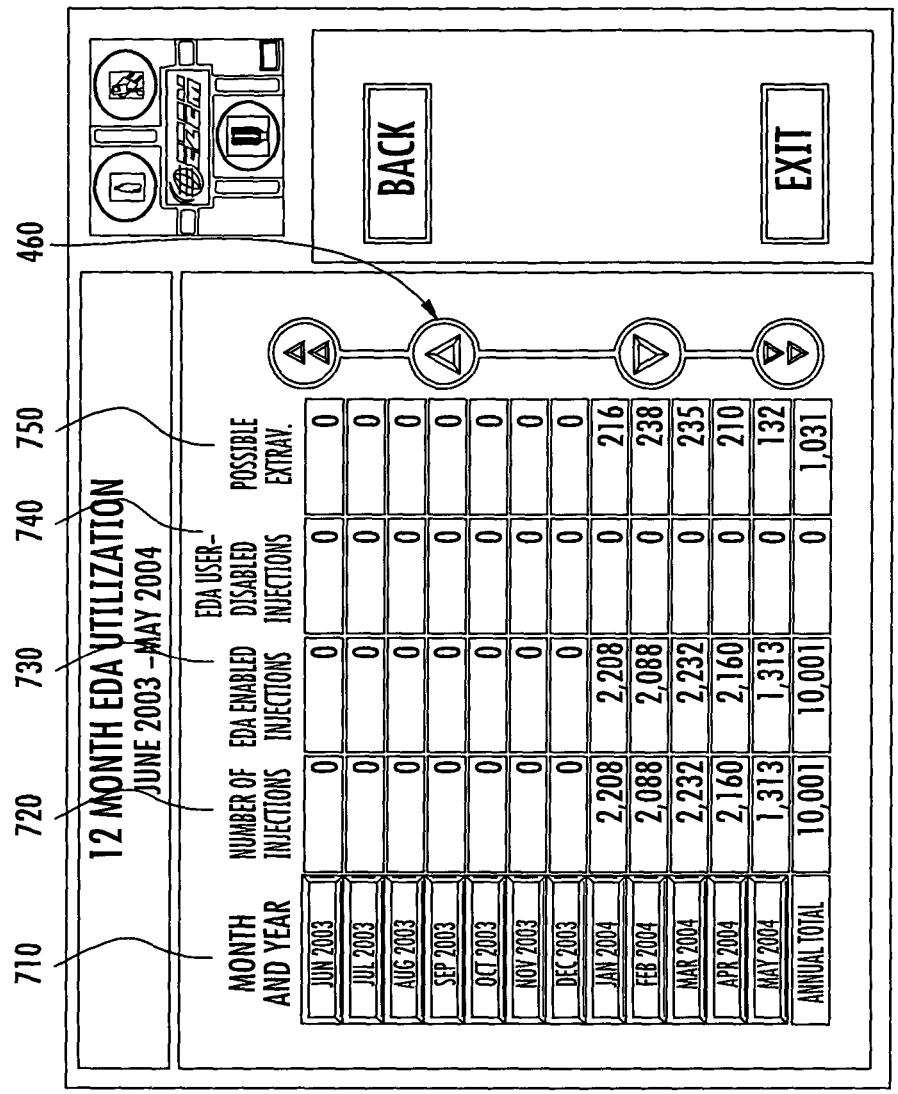
Figure 8:
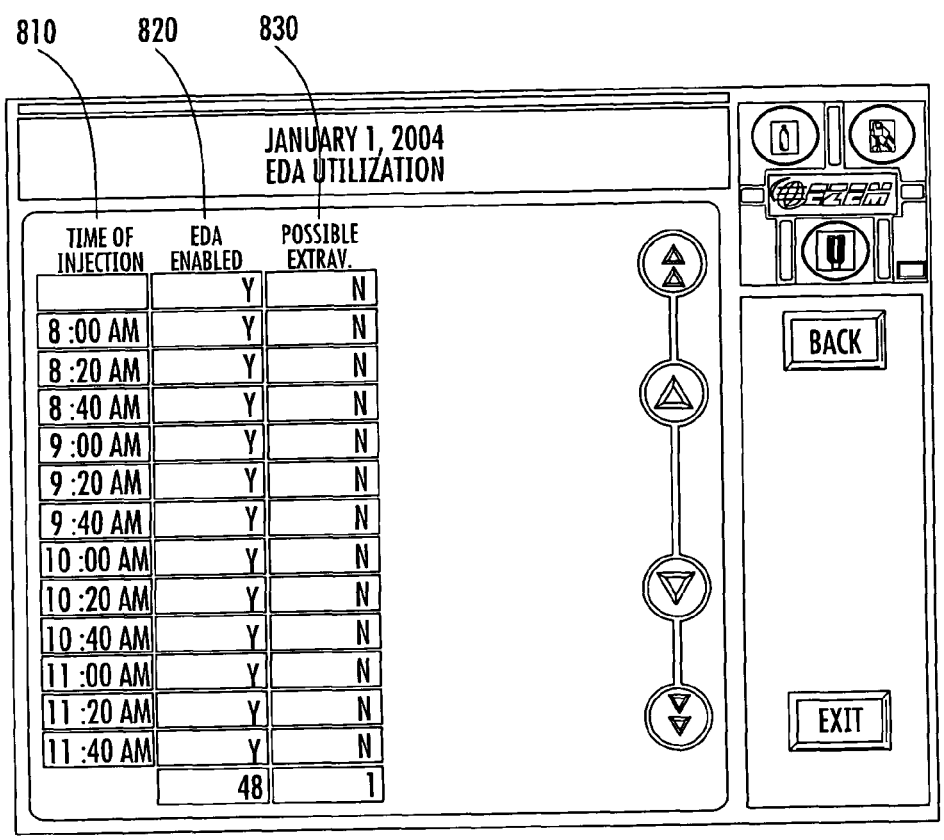
Figure 9:
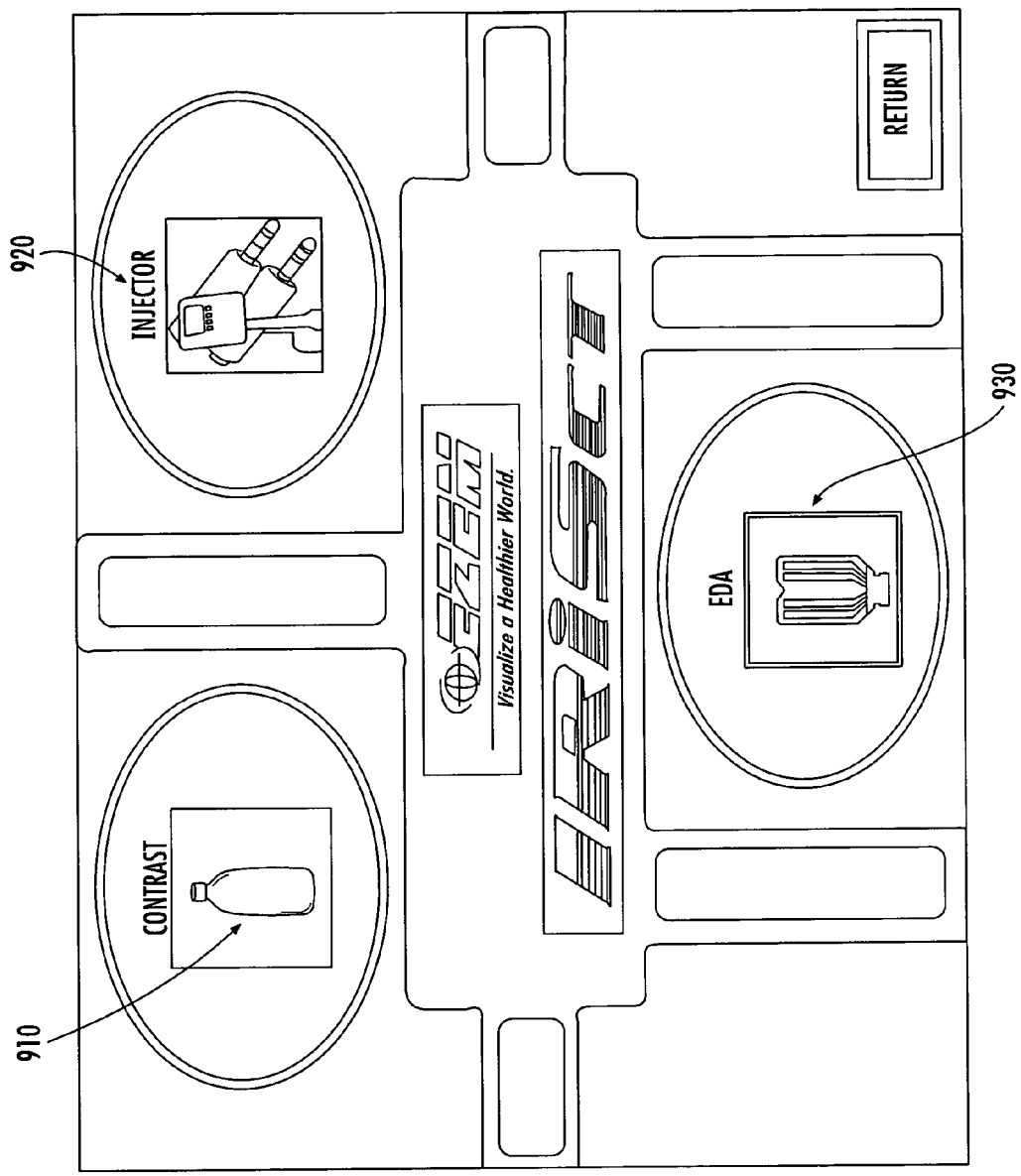

Having thus described the invention in general terms, reference will now be made to the accompanying drawings, which are not necessarily drawn to scale, and wherein:

FIG. 1 shows a non-limiting schematic of a medical imaging suite wherein embodiments of the present invention may be utilized to collect data from a dispensing device capable of dispensing contrast media as part of a medical imaging procedure;

FIG. 2 shows a non-limiting schematic of a data collection device according to one embodiment of the present invention including a controller and a storage device wherein the data collection device is adapted to be capable of communicating with a medical device;

FIG. 3 shows a non-limiting flow chart illustrating the alternative steps of a method for collecting data related to the dispensing of contrast media according to at least one embodiment of the present invention;

FIG. 4 shows a non-limiting schematic of contrast usage data that may be displayed on a user interface according to at least one alternative embodiment of the computer program product of the present invention;

FIG. 5 shows a non-limiting schematic of dispensing device usage data that may be displayed on a user interface according to at least one alternative embodiment of the computer program product of the present invention;

FIG. 6 shows a non-limiting schematic of per-procedure daily dispensing device usage data that may be displayed on a user interface according to at least one alternative embodiment of the computer program product of the present invention;

FIG. 7 shows a non-limiting schematic of extravasation data that may be displayed on a user interface according to at least one alternative embodiment of the computer program product of the present invention;

FIG. 8 shows a non-limiting schematic of per-procedure daily EDA usage data that may be displayed on a user interface according to at least one alternative embodiment of the computer program product of the present invention; and FIG. 9 shows a non-limiting schematic of a display produced by at least one alternative embodiment of the computer program product of the present invention.

DETAILED DESCRIPTION OF THE INVENTION

The present inventions will be further described hereinafter with reference to the accompanying drawings, in which some, but not all embodiments of the invention are shown. Indeed, these inventions may be embodied in many different forms and should not be construed as limited to the embodiments set forth herein. In the figures, like numbers refer to like elements throughout.

While the embodiments of the device, system, method, and computer program product for collecting data related to the dispensing of contrast media are described below in the context of collecting data from dispensing devices and/or EDA devices in a medical imaging suite using powered injectors, it should be understood that the embodiments of the present invention may also be utilized to collect electronic data and/or data log information from a variety of electronic medical devices that may be utilized in a medical procedure or other medical environment. The device, system, method and computer program product embodiments of the present invention may be used for instance, to collect electronic data from a variety of different types of electronic medical devices, such as various dispensing devices or electronic monitoring devices, among others, so as to enable a clinical practice manager or other user to more effectively assess usage and/or efficiency of the particular device and/or consumable accessories or materials used in conjunction with the device.

FIG. 1 shows a non-limiting alternative embodiment of the present invention. Here, a medical imaging device 117 is located within a medical suite 100 (such as a medical imaging suite 100) of a hospital, health care facility, and/or any other facility. The medical imaging device 117 may include, but is not limited to, a computed tomography (CT) scanner, a fluoroscope, a positron emission tomography (PET) scanner, a magnetic resonance (MR) scanner, an ultrasound device and/or other imaging device that may require the dispensing of a contrast media to an individual prior to performing the medical imaging procedure so as to enhance the quality of an image produced by the imaging device 117. As used herein, the term "medical suite" 100 refers generally to a room or collection of rooms within, for instance, a hospital or other health care facility, wherein various components of a medical device (such as a medical imaging system 117, dispensing device 115, EDA 113, or other components) may be located and/or situated in close proximity thereto. The term "medical suite" 100 includes, but is not limited to a medical imaging suite having various components of a medical imaging system located therein and/or in close proximity thereto. The medical suite 100 may further comprise, for example, a control room 120 where an operator of the medical system may be stationed, as well as a procedure room 110 (such as an imaging room 110) wherein the medical device 117 and other equipment related to a medical imaging procedure may be located and/or situated in close proximity thereto (wherein the other equipment may include, but is not limited to a dispensing device 115, configured to be capable of dispensing a contrast media). The dispensing device 115 may comprise various automated dispensing devices suitable for dispensing and/or injecting contrast media prior to a medical imaging procedure. For example, the dispensing device 115 may comprise a power injector device including one or more syringe dispensing systems configured to be capable of injecting an individual with contrast media and/or saline solution prior to a medical imaging procedure, or other medical procedure. One skilled in the art will appreciate that some electronic dispensing devices 115 are capable of collecting, processing, and/or storing data related to a dispensing operation of the dispensing device 115. However, in conventional dispensing devices 115, the data collected is limited to specific codes and/or procedural data that may only be accessed and used by service personnel and/or internal engineering staff. Thus, in one alternative embodiment, the data collection device 200, method and computer program products of the present invention are configured to be capable of accessing and/or storing the data collected by the dispensing device 115 and/or converting it into a usable format that may be effectively presented to a clinician and/or clinical practice manager of a medical suite 100 and/or other medical facility.

FIGS. 1 and 2 show a data collection device 200 according to one alternative embodiment of the present invention wherein the data collection device 200 is adapted to be capable of communicating with a dispensing device 115 configured to be capable of dispensing a contrast media as part of a medical imaging procedure. As shown generally in FIG. 2, the data collection device 200 may comprise, for example, a controller 210 adapted to be capable of communicating with the dispensing device 115, wherein the controller 210 is configured to be capable of transmitting and receiving a usage data set from the dispensing device 115. Furthermore, the controller 210 may be further configured to be capable of arranging, processing, and/or modifying data within the usage data set, wherein the data within the usage data set corresponds to one or more dispensing operations of the dispensing device 115. The data collection device 200 also comprises a storage device 220 configured to be in communication with the controller 210. The storage device 210 may be further configured to be capable of receiving the data within the usage data set such that the data within the usage data set may be selectively retained by the storage device 210 and later retrieved by a user of the data collection device 200. The controller 210 may be further configured to transfer data from one device to another (for example, between medical devices (such as dispensing devices 115) and/or between a dispensing device 115 and a storage device 220). The data collection device 200 may also comprise a user interface 230 configured to be capable of communicating with the storage device 220 and the controller 210 so as to enable a user of the data collection device 200 to selectively access, modify, and supplement the data within the usage data set.

As shown generally in FIG. 1, the data collection device 200 may be configured to be capable of communicating with a medical device such as, for example, a dispensing device 115, EDA 113 (see below), supplemental electronic device (i.e., medical imaging device 117, medical imaging device controller 122, vital sign monitoring devices, blood chemistry analysis device, etc.) and/or other computer devices via a wired and/or wireless computer network 150. Furthermore, in another alternative embodiment of the present invention, the controller 210 of the data collection device 200 may be further adapted to be capable of communicating with an extravasation detection device (EDA) 113 that may be located within the procedure room 110 (such as an imaging room 110) so to be capable of being operably engaged with an individual receiving contrast media from the dispensing device 115. The EDA 113 may also be in communication with the dispensing device 115, data collection device 200, and/or other computer devices via the wired and/or wireless computer network 150. Furthermore, the controller 210 may also be configured to be capable of transmitting and receiving an extravasation data set from the EDA 113 such that the storage device 220 of the data collection device 200 may be further configured to be capable of receiving the data within the extravasation data set such that the extravasation data set may be integrated with the usage data set (from the dispensing device 115, for instance) that may be concurrently retained within the storage device 220 for a given dispensing operation.

As shown in FIG. 1, according to some embodiments of the present invention, the data collection device 200 may be located in the control room 120 of the medical suite 100 and be in communication with the dispensing device 115 via a wire connection extending into the imaging room 110 where the dispensing device 115 may be located. According to some embodiments, the various electronic devices (including, for instance the data collection device 200, dispensing device 115, EDA 113, imaging device 117, imaging device controller 122, computer devices 135, and/or electronic vital sign monitoring devices (EKG devices, breath monitoring devices, pulse monitoring devices, blood flow meters, blood chemistry analysis device, etc.) may also be in communication via a wired and/or wireless computer network 150, as described above. In some alternative embodiments the data collection device 200 may comprise an injector control device that is controlled by the computer program product embodiments of the present invention (as described below, and as shown generally in FIG. 3). In such embodiments, the computer program product may include, but is not limited to, executable portions for collecting a usage data set from the dispensing device 115, and executable portions for directing the usage data set to the storage device 220 of the data collection device 200 (as described more fully below).

As shown generally in FIG. 2, the data collection device 200 may comprise a stand-alone electronic device, including, but not limited to, a personal computer, handheld computer (PDA), electronic tablet, or other device suitable for communicating with the dispensing device 115, EDA 113, imaging device 117, imaging device controller 122, and/or a networked computer 135 (such as, for example, a personal computing device, client or server) via wired and/or wireless connection or by means of a computer network 150. As described above, the data collection device 200 comprises a controller 210 adapted to be capable of communicating with the dispensing device 115, wherein the controller 210 is configured to be capable of transmitting and/or receiving a usage data set from the dispensing device 115. Furthermore, the controller 210 may be further configured to be capable of arranging, processing, and modifying data within the usage data set, wherein the data within the usage data set corresponds to one or more dispensing operations of the dispensing device 115. The controller 210 may comprise a microprocessor chip or other computer device suitable for controlling the collection, processing, and/or arrangement of data. The data collection device 200 may also include, but is not limited to, a storage device 220 configured to be in communication with the controller 210. The storage device 220 may be further configured to be capable of receiving the data within the usage data set such that the data within the usage data set may be selectively retained by the storage device 210 and later retrieved by a user of the data collection device 200. Thus, the storage device 220 may include, but is not limited to, a hard disk drive, memory chip, flash memory device, or other memory device suitable for receiving the data within the usage data set such that the data within the usage data set may be selectively retained and later retrieved by a user of the data collection device 200.

In addition, the data collection device 200 shown in FIG. 2 may further comprise a user interface 230 configured to be capable of communicating with the storage device 220 and the controller 210 so as to enable a user of the data collection device 200 to selectively access, modify, process, and/or supplement the data within the usage data set. According to various alternative embodiments of the present invention, the user interface 230 may include, but is not limited to, a touch screen display, keyboard, mouse device, personal computer, or combinations thereof. Thus, in one alternative embodiment of the present invention, a user may either view, scroll through, annotate, and/or modify data from the usage data set on a touch screen that is operably engaged with and/or integrated with the data collection device 200 or, alternatively, the user may access the data from the data collection device 200 via wire or wireless connections (e.g., via the computer network 150) such that the data may appear on a display or personal computer remotely located from the imaging suite 100, for example. In another alternate embodiment of the present invention, a clinical practice manager may be capable of accessing, viewing, processing, and/or manipulating the data within the usage data set via the computer network 150 such that the data may be visible at a computer 135 located in an administration office 130 located outside the medical suite 100 (as shown generally in FIG. 1).

In another alternative embodiment of the present invention, the controller 210 of the data collection device 200 may be configured to be capable of transmitting and receiving the usage data set comprising various data types that may be associated with the dispensing operation of the dispensing device 115 (or any other related operation) as part of a medical procedure, including but not limited to a medical imaging procedure. For example, such data may include, but is not limited to: a date of the medical imagining procedure; a time of the medical imaging procedure; a quantity of contrast media dispensed; a quantity of contrast media pre-loaded into the dispensing device; the type of contrast media (i.e., ionic or non-ionic); contrast manufacturer and concentration or brand-name; a quantity of a consumable device (such as a syringe) used by the dispensing device; a quantity of saline solution dispensed; and other data categories. The data may also include, but is not limited to, procedure ID numbers, name of stored injection procedure (should actual procedure have be recalled from dispensing device memory), injection protocol (including, for example, phases, flow rates, volume, contrast media type and brand, and/or injection pressure profile, actual or achieved flow rates, actual injection procedure elapsed time, etc.).

According to some embodiments, the data collection device may be configured to be capable of collecting primary data from a dispensing device 115, EDA, 113, imaging device 117, a controller device (which may be in communication with one or more of the various dispensing 115, EDA 113, and/or imaging 117 devices located within a medical imaging suite 100), and/or a computer network 150 (which may be in communication with a database of patient histories and/or administrative data pertinent to a specific procedure and/or dispensing operation). Thus, in one alternative embodiment of the present invention, the data collection device 200 may be further configured to convert the primary data into summary data for use by a clinician and/or administrator. For example, in one embodiment, the primary data may include a number of one or more syringe load-fill-unload cycles arranged by date and time wherein the cycles do not correspond to a dispensing operation, which may correspond, in turn to a summary data point indicating a number syringe pre-filling operations (wherein the dispensing device 115 was used to pre-fill a number of different syringes or other consumable devices with contrast media and/or saline without dispensing the contrast media and/or saline to an individual). Furthermore, such primary data may also include, but is not limited to, a number of one or more syringe load-fill-inject-re-fill cycles arranged by date and time wherein the cycles to not correspond to a removal of the syringe, so as to indicate a summary data point corresponding to a syringe re-use (in, for instances, cases where the syringe was re-filled with contrast media for a second dispensing operation for the same individual).

The data collection device 200 may further be configured to be capable of processing, interrogating, and/or communicating with a computer network 150 of a hospital, medical imaging suite 100, and/or other medical facility such that the data collection device 200 may be further capable of communicating with one/or more medical devices such as, for example, imaging devices 117, imaging device controllers 122, computers 135 and/or other accessory devices that may be located within the medical facility as well as various databases that may be accessible via the network 150. In some cases, the network 150 may be further connected to the internet or to various intranets in order to allow remote access to the data collection device 200 and/or the data set (e.g., a usage data set) collected thereby according to the various device, method, and, computer program product embodiments of the present invention. In such cases, the data may further include, but is not limited to: one or more flow rates, volume, pressure, and programmed pause data corresponding to a dispensing operation; one or more protocol-identifying data corresponding to a pre-programmed dispensing protocol corresponding to a dispensing operation (as collected from one or more dispensing devices 115 in communication with the data collection device via wire or wireless methods and/or via a network 150); one or more individual-identifying and/or individual-specific data (such as patient history information as manually collected by a clinician or administrator using the user interface 230 or as automatically collected by the data collection device 200 via the network 150 from a computer 135 containing a database of patient information); and/or one or more imaging device data corresponding to a medical imaging procedure (as collected from an imaging device 117 or an imaging device controller 122, for instance).

According to various embodiments of the present invention, the computer 135 may receive one or more dispensing device data sets (e.g., usage data sets) from a corresponding one or more of dispensing devices 115 (that may be located in one or more medical imaging suites 100) connected to the network 150. Furthermore, some embodiments of the computer program product (operating on the dispensing device controller 210, for example) may also be executed in a like manner on a computer 135 (which may be co-located with the controller 210 and/or in communication therewith via network 150). Thus, a co-located and/or offsite computer 135 (operated by an administrator, for example) may access all display and operational features associated with the collection device 200, and also may comprise several additional features that may include, but are not limited to: features for automatically synchronizing data sets among the one or more dispensing devices 115 on the network 150 so as to maintain data in a updated format and so as to ensure data formats received from various dispensing devices 115 may be identical to one another; features for assigning user defined names to dispensing devices 115 for easy identification relative to a health care enterprise (for example, location names, code numbers, and/or suite room numbers); features for selectively displaying, editing, or manipulating data from the one or more dispensing devices 115 either individually, in user defined subset by user defined names or aggregate of all dispensing devices 115; features for retaining data sets on computer 135 for archival purposes; features for deploying generic application program interfaces to export dispensing system data to other commercially available generic word processing, spreadsheet and database applications.

Also, in alternative embodiments of the present invention, the data collection device 200 may be configured such that the controller 210 is capable of transmitting and/or receiving the extravasation data set comprising data related to the operation of a medical device such as an EDA 113 as part of a medical procedure, including but not limited to, a medical imaging procedure. Such data collected, processed, and/or stored as part of an extravasation data set may include, but is not limited to: a date of the medical imaging procedure; a time of the medical imaging procedure; an indication of whether or not the extravasation detection device was enabled; an indication of whether or not an extravasation event was detected; and/or an impedance profile corresponding to the detection operation.

The present invention also provides a method for collecting, processing, storing, and/or accessing a data set related to the dispensing of contrast media as part of a medical imaging procedure including, but not limited to, usage data sets. According to one alternative embodiment (as shown generally in FIG. 3), the method may comprise, in step 310, collecting the usage data set from a dispensing device 115, wherein the data within the usage data set is related to a dispensing operation of the dispensing device 115. Furthermore, step 315 may comprise directing the usage data set to a storage device 220 (such as a memory module or other memory component) wherein the storage device 220 is in communication with the dispensing device 115 via a controller 210 and wherein the storage device 220 is configured to be capable of selectively retaining the data within the usage data set.

The methods of the present invention may also comprise, as shown in step 320, collecting an extravasation data set from an EDA 113, wherein the data within the extravasation data set is related to a detection operation of the EDA 113 performed, for example, during a medical procedure, such as a medical imaging procedure. Such a method embodiment may also comprise step 325, which includes, but is not limited to, directing the extravasation data set to the storage device 220 such that the extravasation data set is integrated with the usage data set selectively retained within the storage device 220. Here, the usage data set and extravasation data set collected as part of the method embodiments may contain data of the various types described above in relation to the data collection device 200 embodiments of the present invention.

In another alternative embodiment of the present invention, the method may further comprise additional steps, as shown generally in steps 330 and 335, for collecting a supplemental data set 330 from either a controller 122 configured to control and/or collect data from the imaging device 117 and/or a 135, and for directing the supplemental data set to the storage device 320 such that the supplemental data set is integrated with the usage data set selectively retained within the storage device 220. In some embodiments, as described above with respect to the data collection device 200 and system embodiments of the present invention, the supplemental data set collected as part of step 330 may be collected from a database and/or computer network 150 that may be in communication (via wired or wireless methods) with a computer 135. Thus, the supplemental data set may include, but is not limited to, data related to an individual patient history, insurance information, consumable device inventory information, and/or other data (including clinical site and/or medical imaging suite 100 identifying information) that may be stored in a database residing on a remote computer 135 and/or other electronic device in communication with the network 150. Thus, according to one alternative embodiment of the present invention, a clinical practice manager may access, review, process, and/or supplement the data within the supplemental data set and/or the more inclusive usage data set via a remote computer 135 located in a remote location such as an administrative office 130 (as shown schematically in FIG. 1).

Furthermore, a clinical practice manager (or other operator) may, via the computer 135 for example, copy, transfer, and/or create backup copies of the data sets (e.g., usage data sets) and/or supplemental data sets for archival storage and/or for subsequent download to one or more dispensing devices 115 and/or supplemental devices that may require refurbishment, replacement, and/or memory replacement.

Other alternative embodiments of the present invention may further comprise the additional steps 340, 350, and 360 as shown in FIG. 3. Here, step 340 may comprise directing a portion of the data within the usage data set corresponding to one or more individual medical imaging procedures into one or more procedure data subsets, each corresponding to an individual medical imaging procedure. Thus, step 340 may comprise arranging the data according to procedure ID, procedure time and date, and/or imaging practice accession number such that the various data from the usage data set and/or extravasation data set corresponding to a given dispensing procedure may be collected and arranged according to the specific time and date (as shown in step 350) in which the dispensing operation and/or medical imaging procedure occurred. In addition, the method may further comprise step 360 which includes displaying data within the usage data set to a user via a user interface 230 configured to be capable of communicating with the storage device 220 and the controller 210.

The present invention may be utilized to collect and/or arrange usage data and/or extravasation data from a dispensing device 115, EDA 113, imaging devices 117, and/or other computer devices 135 (such as personal computers) in communication with a network 150 such that the data may be compiled into a per-procedure format (as shown generally in FIG. 6, such that a clinical practice manager may selectively access such data from a remote location (such as an administrative office 130), via a computer 135 in communication with a computer network 150 that is in communication with the data collection device 200 of the present invention. The method embodiments may thus allow a clinical practice manager to more easily gain access (via a stand-alone data collection device 200, a networked (remote and/or via an intranet) computer 135, and/or another electronic device that may be in communication with the storage device 220) to detailed usage data related to the utilization of the various devices, inventoried consumables, and contrast media that may be used in a conventional medical imaging suite 100.

The present invention may also provide a computer program product embodiment capable of executing the various method steps 310-360 (as shown generally in FIG. 3). In one alternative embodiment, the computer program product embodiments of the present invention are capable of controlling a data collection device 200 (such as the stand-alone device 200 shown generally in FIG. 2, or the dispensing device 115 controller 200 shown in FIG. 1) comprising a controller 210 and a storage device 220, wherein the data collection device 200 is adapted to be capable of communicating (via a computer network 150 or other wire or wireless methods) with a dispensing device 115 configured to be capable of dispensing a contrast media as part of a medical imaging procedure. The computer program product of the present invention may be capable of operating in conjunction with an operating system (including, but not limited to, Windows, Linux, and/or other operating systems known in the art) that may be used as the base operating system for the data collection device 200, dispensing device controller, personal computers, and/or other electronic devices configured to be capable of communicating via the computer network 150 within the medical suite 100 and beyond. The computer program product of the present invention may comprise an executable portion for collecting a usage data set from a dispensing device 115, wherein the data within the usage data set is related to a dispensing operation of the dispensing device 115. A non-limiting example of this executable portion is shown in general schematic form as step 310 in FIG. 3 (showing also some various alternative method embodiments of the present invention.) This executable portion may further comprise the capability for determining one or more values related to the usage of the dispensing device 115. For example, the dispensing device 115 may store usage data including the volume of contrast media that is pre-loaded into a sterile disposable syringe for a given dispensing operation as well as data corresponding to the amount of contrast media actually dispensed via the disposable syringe during the same operation. Thus, in one alternative embodiment of the present invention, the executable portion shown in step 310 of FIG. 3 may include mathematically determining the amount of contrast media that was left over in the disposable syringe following the specific procedure. This data may, in turn become part of the data set (e.g., a usage data set) that is stored, for example, in the memory device 220 in the data collection device 200 of the present invention.

The computer program product of the present invention may also include an executable portion for directing the usage data set to the storage device 220 of the data collection device 200 (as shown schematically in step 315 of FIG. 3) wherein the storage device 220 is in communication with the dispensing device 115, and wherein the storage device is configured to be capable of selectively retaining the data within the usage data set. Thus, according to the executable portion shown in step 315, the computer program product of the present invention may be capable of storing and/or accumulating usage data over time, so as to be capable of producing summary usage data reports for one or more dispensing devices 115 that may be present within a given imaging suite 100. Non limited examples of such reports are shown generally in FIGS. 4-8 and discussed in detail below.

As discussed above, the data collection device 200 may be in communication with one or more extravasation detection devices (EDA) 113 that may be used in conjunction with the dispensing device 115 in a given dispensing operation to detect possible extravasation events in individuals receiving contrast media intravenously or arterially via a dispensing device 115 such as a power injector. The EDA 113 may also generate an extravasation data set corresponding to a given dispensing operation. Thus, computer program product embodiments of the present invention may also comprise an executable portion (as shown generally in FIG. 3 as step 320) for collecting an extravasation data set from an EDA 113, wherein data within the extravasation data set is related to a detection operation of the extravasation detection device performed during a dispensing operation and/or medical imaging procedure. As described above, EDA 113 may include an impedance detection transducer that generally produces data related to the impedance detected near an injection site on the skin of an individual to detect the occurrence of extravasation events. Thus, the executable portion of step 320 may comprise collecting relatively simple extravasation data, including, for instance, an indication of whether or not the EDA 113 was enabled for a given medical procedure, such as a dispensing operation, an indication of whether or not the EDA 113 detected an extravasation event during a given medical procedure, such as a dispensing operation, and, in some cases data related to the impedance values (or other values related to the sensing method used to detect an extravasation event, including, but not limited to, ultrasound, low-dose x-ray, and/ or other techniques) detected by the EDA 113 during a given medical procedure, such as a dispensing operation. According to some embodiments, the computer program product embodiments of the present invention may also comprise an executable portion (shown in step 325 of FIG. 3) for directing the extravasation data set described above to the storage device 220 of the data collection device 200 such that the extravasation data set is integrated with the usage data set selectively retained within the storage device 220. Thus, the executable portion shown in step 325 may further comprise synchronizing (by, for example the time/date stamp and/or procedure ID) the extravasation data set with a given usage data set for a particular dispensing operation such that both extravasation data and usage data pertaining to a given dispensing operation may be presented in a cohesive summary format (as shown generally in FIG. 6 (discussed below)).

As discussed above, the data collection device 200 may be in communication with one or more alternate electronic devices that may be used in conjunction with the dispensing device 115 during a medical procedure (e.g., a medical imaging procedure) conducted within a medical imaging suite 100 and that may also produce a supplemental data set corresponding to a particular dispensing operation and/or particular medical imaging procedure. Such electronic devices may include, for instance, one or more medical imaging devices 117, one or more medical imaging device controllers 122 (that may be co-located with the medical imaging device 117 and/or remotely located in a control room 120 as shown in FIG. 1), computers 135 (such as a PC located in an administrative office 130 located remotely from the medical imaging suite 100 or a server computer also located remotely from the imaging suite 100), and/or other electronic devices that may generate supplemental data of the various types described above in conjunction with a dispensing operation and/or medical imaging procedure. Thus, computer program product embodiments of the present invention may also comprise an executable portion (as shown generally in FIG. 3 as step 330) for collecting a supplemental data set one or more of the devices described above, wherein data within the supplemental data set is related to a operation of the devices above during a dispensing operation and/or medical imaging procedure. Thus, the executable portion of step 330 may comprise, for instance, collecting supplemental data related to the operation of the imaging device 117 during a given imaging procedure, collecting supplemental data related to the individual (patient ID, medical history, etc) being imaged in according with a specific medical imaging procedure (i.e., from a database accessible via the computer network 150), collecting information from an imaging device controller 122 (such as clinician ID, data related to a pre-programmed imaging routine, data related to the energy level and type used to complete the imaging procedure, and/or other imaging-related data), and/or collecting data from one or more other electronic devices that may be accessible and/or interrogable via the computer network 150 or via other communication methods that will be appreciated by one skilled in the art. According to some embodiments, the computer program product embodiments of the present invention may also comprise an executable portion (shown in step 335 of FIG. 3) for directing the supplemental data set described above to the storage device 220 of the data collection device 200 such that the supplemental data set is integrated with the usage data set selectively retained within the storage device 220. Thus, the executable portion shown in step 335 may further comprise synchronizing (by, for instance the time/date stamp and/or procedure ID) the supplemental data set with a given usage data set for a particular dispensing operation and/or medical imaging procedure such that both supplemental data and usage data pertaining to a given dispensing operation and/or medical imaging procedure may be presented in a cohesive summary format to a clinical practice manager and/or physician according to the various embodiments of the present invention (as shown generally in FIG. 6 (discussed below)).

As shown in step 340 of FIG. 3, the computer program product of the present invention may further comprise an executable portion for directing a portion of the data within the usage data set corresponding to one or more individual medical imaging procedures into one or more procedure data subsets, each corresponding to an individual medical imaging procedure. Thus, as discussed generally above, usage data corresponding to an individual dispensing operation/imaging procedure may be partitioned from the mass of data taken in by a particular dispensing device 115 and/or EDA 113. The executable portion of step 340 may further comprise selecting data from the usage data set corresponding to a particular procedure ID and/or a particular time/date stamp such that usage data may be compiled on a per-procedure basis and displayed as such using the executable portion for displaying discussed below in relation to Step 360 and FIGS. 4-9. The output of the executable portion of step 340 thus provides a per-procedure array of usage data.

The computer program product of the present invention may also comprise an executable portion shown generally as a non-limited example in step 350 for arranging the one or more procedure data subsets by a date of the medical imaging procedure. Here, in one example, the usage data may be compiled into summary form based on the date/time of a given dispensing operation/imaging procedure. In this manner, the computer program product may also provide a user with, for instance, a monthly total of usage data (such as the total amount of contrast media used, total number of injections performed, etc) via a user interface 230 of the data collection device 210 as shown generally in FIGS. 4-6.

As shown in step 360, the computer program product of the present invention may also comprise an executable portion for displaying data within the usage data set to a user via a user interface 230 adapted to be capable of communicating with the storage device 210 and the controller 220. For example, the executable portion of step 360 may further comprise displaying (via the user interface 230, for instance) a navigation display such as that shown in FIG. 9 wherein a user may choose to view usage data related to the dispensing device 115 (injector) utilization, usage data related to contrast media utilization, and/or usage data related to the EDA 113. As shown in FIG. 9, according to some embodiments, the executable portion of step 360 may comprise displaying the navigation display on a touch screen user interface 230 such that a user may select either the contrast button 910, the injector button 920, or the EDA button 930 corresponding to the various summary views of the usage data described generally above.

For instance, according to some embodiments, if the user were to touch the contrast button 910 an annual contrast utilization screen (ending with the current month) could be displayed in accordance with the executable portion of step 360, as shown generally in FIG. 4. Several data fields may be displayed, including, but not limited to, Month and Year 410, monthly total of pre-loaded contrast media 420, monthly total of dispensed contrast media 430, residual contrast media volume 440 (obtained by, for instance the executable portion of step 310, wherein the monthly total of dispensed contrast media 430 may be subtracted from the monthly total of pre-loaded contrast media 420. In addition, the average contrast media volume dispensed for the month 450 may also be displayed. According to the various computer program embodiments of the present invention, a user may navigate to more day-specific data by pressing the time/date buttons 400 corresponding to the month of interest which will cause the data collection device 200 to display similar summary data fields corresponding to the days of the selected month. In addition, the user may scroll back and forward in time using the arrow navigation buttons 460 displayed on the user interface 230.

In another alternative embodiment of the present invention, if the user selects a given month and subsequently a given day using the time/date button 400 (pressed once to select a given month, and again to select a given day), the computer program product (according to the executable portion of step 360 will display procedure-specific usage data arranged by the time of the procedure/dispensing operation on the selected day. Such usage data is thus specific to a given dispensing operation and represents procedure-specific usage data sets generated by the executable portion of step 340. The usage data collected for a given procedure may include the same data fields shown in items 420, 430, 440, and 450 as discussed above.

Alternatively, as shown in the navigation display shown in FIG. 9, a user may opt to view usage data related to the dispensing device 115 by pressing the injector button 920 which would, in turn enable the computer program product to display monthly usage data on the user interface 230 as shown in FIG. 5. The usage data displayed, according to one embodiment, includes, month and year 510, number of dispensing operations 520, number of contrast injections 530 (which may be a subset of dispensing operations, which may include saline injections or other dispensing operations), number of contrast/saline injections, and number of disposable syringes utilized (as determined by the data collecting executable portion of step 310). As discussed previously with regard to contrast media usage data screen (FIG. 4), a user may press one of the time/date buttons to call up more specific daily usage data corresponding to the dispensing device 115. Within the daily usage data summaries, the user may again press the time/date button in order to access all of the usage data summaries corresponding to individual dispensing operations (as shown generally in FIG. 6.) As shown in FIG. 6, the usage data shown may include, but is not limited to, time/date stamp 610, average dispensing rate 620 (i.e., contrast media flow rate average for the dispensing operation), contrast media volume 630, saline flow rate 640 (which is 0.0 if not used), saline volume 650, average dispensing pressure 660, maximum dispensing pressure 670, indication of whether EDA 113 was enabled 680 (which is a binary, yes/no data point), and an indication of whether an extravasation event was detected by the EDA 113 (which also represents a binary, yes/no data point). Similarly, the data fields may be expanded to include association of contrast type, concentration, and/or brand. The user may also navigate through the display of FIG. 6 using the scroll arrows 460 which allow the user to scroll back and forward in time. In addition, the user may press the time button 600 in order to access specific data about the types and relative volumes of the various contrast media that may have been pre-loaded into the dispensing device 115/syringe for that specific procedure. In addition, as shown in FIG. 6, the maximum dispensing pressure 605 button may be depressed for a given dispensing operation which will enable the user interface 230 to display the pressure profile (i.e., the dispensing pressure over time) exerted by the dispensing device 115 over the course of the selected dispensing operation. According to some alternative embodiment, the depression of the maximum dispensing pressure button 605 may further trigger the display (in a pop-up display, for instance) of the pressure plot and/or other contrast media phase information dispensed as part of a particular procedure.

In addition, as shown in the navigation display shown in FIG. 9, a user may choose to view usage data related to the EDA 113 by pressing the injector button 920 which would, in turn enable the computer program product to display monthly usage data corresponding to the EDA 113 on the user interface 230 as shown in FIG. 7. The usage data displayed, according to one embodiment, includes, month and year 710 of EDA 113 usage, the number of dispensing operations for the month 720, the number of dispensing operations for which an EDA 113 was enabled 730, the number of dispensing operations for which an EDA 113 was not enabled 740, and the number of extravasation events detected by the EDA 113. As in the displays discussed above (see FIGS. 4 and 5), the user may opt to scroll through a number of time periods (using the scroll arrows 460), and/or the user may enable the computer program product (via the display executable portion of step 360) to display day-specific and/or procedure specific extravasation data generated by the EDA 113 and collected (according to the executable portion of step 320) by the data collection device 200. For example, as shown generally in FIG. 8, the user may choose (by pressing the time/date buttons 700) to view extravasation data corresponding to specific procedures (arranged by time, for example). Such extravasation data may include, but is not limited to, a binary yes/no corresponding to EDA 113 enablement 820, as well as a binary yes/no corresponding to the detection of an extravasation event. In other alternative embodiments of the present invention, the user may press a button corresponding to a specific binary data point in the extravasation event data column 830 to access a detailed plot of the impedance profile generated by the EDA 113 in the specific dispensing operation (which led, in turn, to the triggering of a "yes" data point for an extravasation event).

While the displaying executable portions of step 360 above are shown in terms of a touch-screen user interface 230 as discussed above, the data screens above may also be navigated by other means, including "point-and-click" methods (via a computer mouse, trackpad, and/or other methods that may be appreciate by one skilled in the art). Furthermore, in some embodiments, the user interface 230 may be in communication with a printer, monitor, or other electronic device suitable for displaying and/or printing the usage data collected and/or stored in accordance with the various methods of the present invention.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Throughout the description, where devices, systems, and computer program products are described as having, including, or comprising specific components, or where processes or methods are described as having, including, or comprising specific process or method steps, it is contemplated that devices, systems, and/or computer program products of the present invention may also consist essentially of, or consist of, the recited components, and that the methods of the present invention may also consist essentially of, or consist of, the recited method steps. Further, it should be understood that the order of steps or order for performing certain actions are immaterial so long as the invention remains operable. Moreover, two or more steps or actions may be conducted simultaneously.

The content of each of the patent and non-patent documents referred to herein is expressly incorporated herein by reference in its entirety.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Also, the invention may suitably comprise, consist of, or consist essentially of the elements or method steps described herein. Further, the invention described herein suitably may be practiced in the absence of any element or process step which is or is not disclosed herein.

That which is claimed:

1. A system configured for communication between a plurality of medical devices, the system comprising:
    a dispensing device configured for dispensing a contrast media as part of a medical procedure;
    a controller configured for communicating with the dispensing device and for receiving a data set from the dispensing device, the controller being further configured for sorting and modifying the data within the data set and for partitioning the data within the data set into procedure data subsets corresponding to individual dispensing operations, the data within the data set being related to contrast usage and to dispensing operations performed by the dispensing device;
    a storage device configured to be in communication with the controller, the storage device further configured for receiving the data within the data set such that the data within the data set may be selectively retained by the storage device;
    one or more electronic devices, the one or more electronic devices including a medical imaging device and a medical imaging device controller associated with the medical imaging device;
    a graphical user interface configured for communicating with the storage device and the controller so as to enable a user to selectively access, modify, and supplement the data within the data set with patient data related to a recipient of the contrast media;
    the controller further configured for communicating with the one or more electronic devices, the controller being further configured for receiving a supplemental data set from the one or more electronic devices, the controller further configured for compiling the data within the supplemental data set with the data from the dispensing device,
    the controller further configured for displaying a navigation display on the graphical user interface, the navigation display comprising a contrast button and a dispensing device button, wherein the controller is further configured to display a chronological summary of contrast usage data on the graphical user interface when the user selects the contrast button and to display a chronological summary of dispensing device operations data on the graphical user interface when the user selects the device dispensing button; and
    wherein the chronological summary of contrast usage data further comprises a plurality of time buttons each corresponding to a non-overlapping period of time within the period of time for which the contrast usage data is displayed in the chronological summary, and wherein, when the user selects one of the time buttons, the controller is further configured to display the contrast usage data for the period of time corresponding to the selected time button.

2. A system according to claim 1, wherein the one or more electronic devices include an extravasation detection device, wherein the supplemental data set comprises an extravasation data set, wherein the navigation display further comprises an extravasation detection device button, and wherein the controller is further configured to display a chronological summary of extravasation data when the user selects the extravasation detection button.

3. A system according to claim 1, wherein the one or more electronic devices comprise one or more of the following:
    (i) medical imaging devices in addition to the medical imaging device;
    (ii) medical imaging device controllers in addition to the medical imaging device controller associated with the medical imaging device;
    (iii) vital sign monitoring devices;
    (iv) blood chemistry analysis devices;
    (v) computer devices; and
    (vi) combinations thereof.

4. A system according to claim 1, wherein the controller is operably engaged with the dispensing device.

5. A system according to claim 2, wherein the controller is configured for communicating with the dispensing device and the extravasation detection device via a computer network.

6. A system according to claim 1, wherein the controller is configured for transmitting and receiving the data set comprising data selected from a group consisting of:
    (i) a date of the medical imaging procedure;
    (ii) a time of the medical imaging procedure;
    (iii) a quantity of contrast media dispensed;
    (iv) a quantity of contrast media pre-loaded into the dispensing device;
    (v) a quantity of a consumable devices used by the dispensing device;
    (vi) a quantity of saline solution dispensed;
    (vii) a time and pressure history related to the dispensing operation;
    (viii) a number of one or more syringe load-fill-unload cycles arranged by date and time wherein the cycles do not correspond to the dispensing operation, so as to indicate a syringe pre-filling operation;
    (ix) a number of one or more syringe load-fill-inject-re-fill cycles arranged by date and time wherein the cycles to not correspond to a removal of a syringe, so as to indicate a syringe re-use;
    (x) one or more of flow rate, volume, pressure, and programmed pause data corresponding to a dispensing operation;
    (xi) one or more protocol-identifying data corresponding to a pre-programmed dispensing protocol corresponding to a dispensing operation;
    (xii) one or more individual-identifying data;
    (xiii) one or more imaging device data corresponding to a medical imaging procedure;
    (xiv) one or more contrast media data; and
    (xv) combinations thereof.

7. A system according to claim 2, wherein the controller is configured for transmitting and receiving the extravasation data set comprising data selected from a group consisting of:
    (i) a date of the medical imaging procedure;
    (ii) a time of the medical imaging procedure;
    (iii) an indication of whether or not the extravasation detection device was enabled;
    (iv) an indication of whether or not an extravasation event was detected;
    (v) an impedance profile corresponding to the detection operation; and
    (vi) combinations thereof.

8. A system for collecting data related to the dispensing of contrast media comprising:
- a dispensing device configured for dispensing a contrast media as part of a medical imaging procedure;
- a controller configured for communicating with the dispensing device;
- a data set received by the controller from the dispensing device, data within the data set being related to contrast usage and dispensing operations performed by the dispensing device;
- a storage device configured for receiving the data within the data set such that the data within the data set may be selectively retained by the storage device;
- one or more electronic devices, the one or more electronic devices including a medical imaging device and a medical imaging device controller associated with the medical imaging device;
- a graphical user interface configured for communicating with the storage device and the controller so as to enable a user to selectively access, modify, and supplement the data within the data set with patient data related to a recipient of the contrast media;
- the controller further configured for partitioning the data within the data set into procedure data subsets corresponding to individual dispensing operations, the controller further configured for communicating with the one or more electronic devices, the controller being further configured for transmitting and receiving a supplemental data set to and from the one or more electronic devices;
- the controller being further configured for compiling the data within the supplemental data set with the data from the dispensing device into a per procedure format, and wherein the controller is further configured for creating a summary of the compiled data for a user in which the data from the dispensing device is presented in combination with the data within the supplemental data set from the one or more electronic devices in a per procedure format;
- the controller further configured for displaying a navigation display on the graphical user interface, the navigation display comprising a contrast button and a dispensing device button, wherein the controller is further configured to display a chronological summary of contrast usage data over a period of time on the graphical user interface when the user selects the contrast button and to display a chronological summary of dispensing device operations data on the graphical user interface when the user selects the device dispensing button; and
- wherein the chronological summary of contrast usage data further comprises a plurality of time buttons each corresponding to a non-overlapping period of time within the period of time for which the contrast usage data is displayed in the chronological summary, and wherein, when the user selects one of the time buttons, the controller is further configured to display the contrast usage data for the period of time corresponding to the selected time button.

9. A system according to claim 8, wherein the one or more electronic devices further include an extravasation detection device, and wherein the supplemental data set comprises an extravasation data set, wherein the navigation display further comprises an extravasation detection device button, and wherein the controller is further configured to display a chronological summary of extravasation data when the extravasation detection device button is selected by the user.

10. A system according to claim 8, wherein the one or more electronic devices are chosen from the group consisting of:
   (i) medical imaging devices;
   (ii) medical imaging device controllers;
   (iii) vital sign monitoring devices;
   (iv) blood chemistry analysis devices;
   (v) computer devices; and
   (vi) combinations thereof.

11. A system according to claim 8, wherein the controller is operably engaged with the dispensing device.

12. A system according to claim 8, further comprising an extravasation detection device, wherein the controller is configured for communicating with the dispensing device and the extravasation detection device via a computer network.

13. A system according to claim 8, wherein the controller is configured for transmitting and receiving the data set comprising data selected from a group consisting of:
   (i) a date of the medical imagining procedure;
   (ii) a time of the medical imaging procedure;
   (iii) a quantity of contrast media dispensed;
   (iv) a quantity of contrast media pre-loaded into the dispensing device;
   (v) a quantity of a consumable devices used by the dispensing device;
   (vi) a quantity of saline solution dispensed;
   (vii) a time and pressure history related to the dispensing operation;
   (viii) a number of one or more syringe load-fill-unload cycles arranged by date and time wherein the cycles do not correspond to the dispensing operation, so as to indicate a syringe pre-filling operation;
   (ix) a number of one or more syringe load-fill-inject-re-fill cycles arranged by date and time wherein the cycles to not correspond to a removal of a syringe, so as to indicate a syringe re-use;
   (x) one or more of flow rate, volume, pressure, and programmed pause data corresponding to a dispensing operation;
   (xi) one or more protocol-identifying data corresponding to a pre-programmed dispensing protocol corresponding to a dispensing operation;
   (xii) one or more individual-identifying data;
   (xiii) one or more imaging device data corresponding to a medical imaging procedure;
   (xiv) one or more contrast media data; and
   (xv) combinations thereof.

14. A system according to claim 9, wherein the controller is configured for transmitting and receiving the extravasation data set comprising data selected from a group consisting of:
   (i) a date of the medical imaging procedure;
   (ii) a time of the medical imaging procedure;
   (iii) an indication of whether or not the extravasation detection device was enabled;
   (iv) an indication of whether or not an extravasation event was detected;
   (v) an impedance profile corresponding to the detection operation; and
   (vi) combinations thereof.

15. The system according to claim 1, wherein the chronological summary of contrast usage data comprises a display of total pre-loaded contrast media, total dispensed contrast media, and total residual contrast media, for various time periods displayed in chronological order.

16. The system according to claim 1 wherein the chronological summary of dispensing device operations data comprises a display of number of dispensing operations, number of contrast injections, number of contrast/saline injections, and number of syringes utilized, for various time periods displayed in chronological order.

17. The system according to claim 2 wherein the chronological summary of extravasation data comprises a display of number of dispensing operations, number of dispensing operations for which extravasation detection was enabled, the number of dispensing operations for which extravasation detection was not enabled, for various time period displayed in chronological order.

18. The system according to claim 8, wherein the chronological summary of contrast usage data comprises a display of total pre-loaded contrast media, total dispensed contrast media, and total residual contrast media, for various time periods displayed in chronological order.

19. The system according to claim 8 wherein the chronological summary of dispensing device operations data comprises a display of number of dispensing operations, number of contrast injections, number of contrast/saline injections, and number of syringes utilized, for various time periods displayed in chronological order.

20. The system according to claim 9 wherein the chronological summary of extravasation data comprises a display of number of dispensing operations, number of dispensing operations for which extravasation detection was enabled, the number of dispensing operations for which extravasation detection was not enabled, for various time period displayed in chronological order.

21. The system according to claim 8 wherein each non-overlapping period of time comprises one month.

* * * * *